May 20, 1952 H. SEELER Re. 23,496

RESUSCITATOR

Original Filed Feb. 26, 1951 3 Sheets-Sheet 1

INVENTOR.
HENRY SEELER
BY Wade Koontz AND
ATTORNEY
Charles L. Burgoyne
AGENT

RESUSCITATOR

Original Filed Feb. 26, 1951 3 Sheets-Sheet 2

INVENTOR.
HENRY SEELER
BY Wade Kourth AND ATTORNEY
Charles L. Burgoyne AGENT

RESUSCITATOR
Original Filed Feb. 26, 1951 3 Sheets-Sheet 3
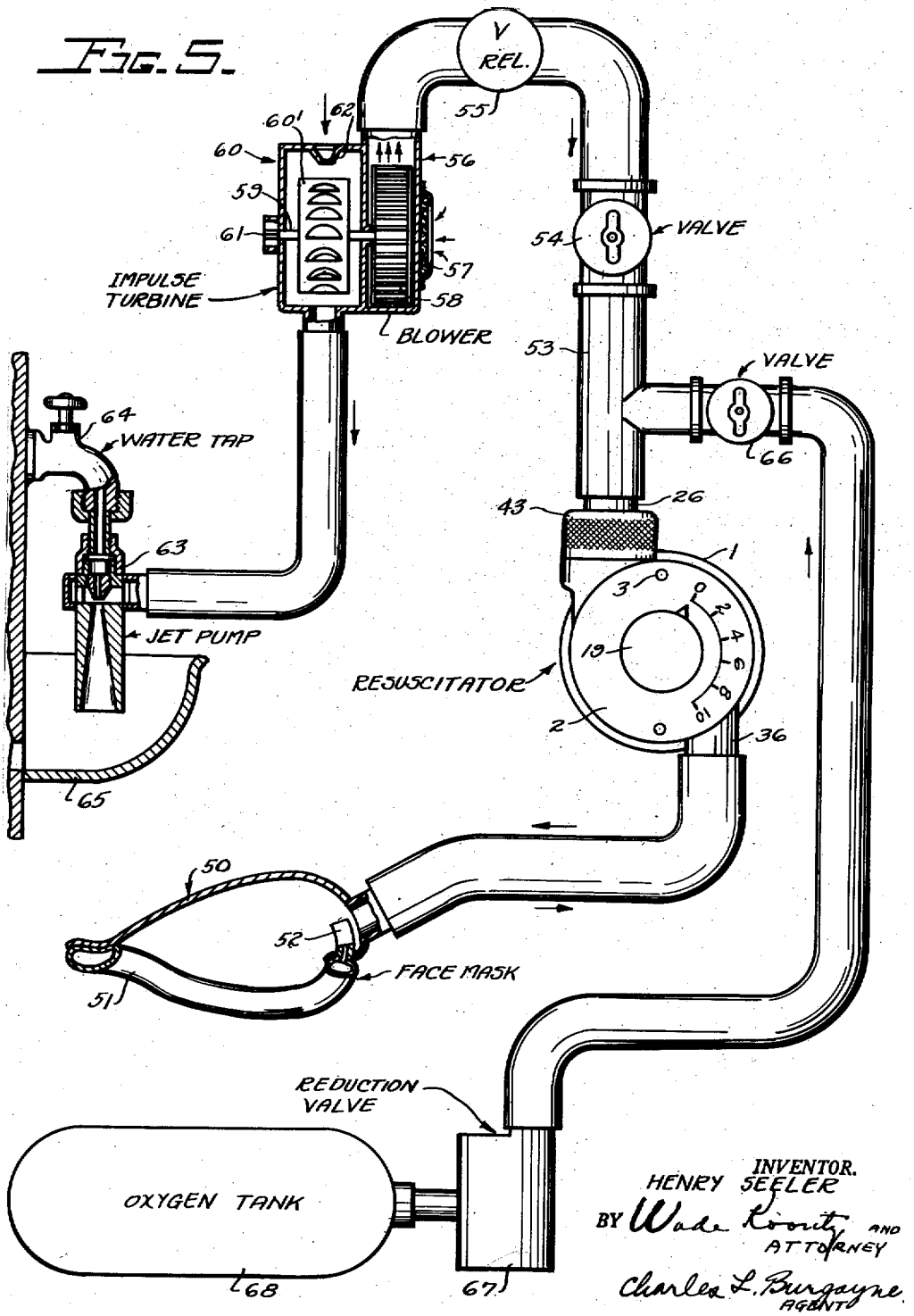
INVENTOR.
HENRY SEELER
BY Wade Koontz AND
ATTORNEY
Charles L. Burgayne
AGENT Reissued May 20, 1952

Re. 23,496

UNITED STATES PATENT OFFICE 23,496

RESUSCITATOR

Henry Seeler, Dayton, Ohio

Original No. 2,581,450, dated January 8, 1952, Serial No. 212,818, February 26, 1951. Application for reissue February 15, 1952, Serial No. 271,841

7 Claims. (Cl. 128—29)

(Granted under the act of March 3, 1883, as amended April 30, 1928; 370 O. G. 757)

Matter enclosed in heavy brackets [ ] appears in the original patent but forms no part of this reissue specification; matter printed in italics indicates the additions made by reissue.

The invention described herein may be manufactured and used by or for the United States Government for governmental purposes without payment to me of any royalty thereon.

The present invention relates to a resuscitator or artificial respiration device of simple, compact and reliable construction.

The primary object of the invention is to provide a resuscitator of the kind which includes an aspirator into which flows a gas under pressure suitable for use in resuscitating human patients and wherein a crank actuated butterfly valve within the aspirator is automatically moved from an open position to a closed position and vice versa by the action of a pressure responsive means coupled to an overcenter spring means associated with the crank actuated valve, whereby the valve when open allows gas to flow through the aspirator to produce a suction effect and when closed causes gas to flow laterally from the aspirator to produce a pressure effect.

A further object of the invention is to provide a resuscitator of the kind which includes an aspirator or Venturi tube into which flows a gas under pressure suitable for use in resuscitating human patients, wherein a butterfly valve in the aspirator downstream from a lateral opening therein is rigidly connected to a simple crank operating means, wherein a coil spring connected to the crank operating means is actuated by a slidably mounted rod fixed to a diaphragm, wherein adjustable compression springs are provided at opposite ends of the slidably mounted diaphragm actuated rod and wherein a gas flow channel in the resuscitator is in communication with the lateral opening in the aspirator, with a tube leading to a face mask and with one side of the rod-actuating diaphragm, whereby the butterfly valve when brought to open position by the diaphragm and slidably mounted rod acting through the coil spring and crank operating means functions to produce the exhalation phase of the resuscitation cycle and when brought to closed position functions to produce the inhalation phase of the resuscitation cycle.

Another object of the invention is to provide a resuscitator system including a face mask and associated resuscitator which receives its supply of gas from a pressurized oxygen source or from a blower operated by an impulse turbine, and wherein the turbine operates by the inflow of atmospheric air by virtue of negative back pressure on the turbine achieved by use of a simple jet pump operable by a water tap.

Another object of the invention is to provide a resuscitator of the kind which includes an aspirator or Venturi tube into which flows a gas under pressure and including a control valve in the aspirator located downstream from a lateral opening therein and wherein the control valve is operable automatically by a simple and reliable mechanism actuated by a pressure responsive diaphragm.

The above and other objects of the invention will become apparent upon reading the following detailed description in conjunction with the accompanying drawings, in which:

Fig. 5 is a schematic view of resuscitator and associated components comprising a possible system for general use in hospitals, aid stations and related installations.

RESUSCITATOR CONSTRUCTION

Figure 1:
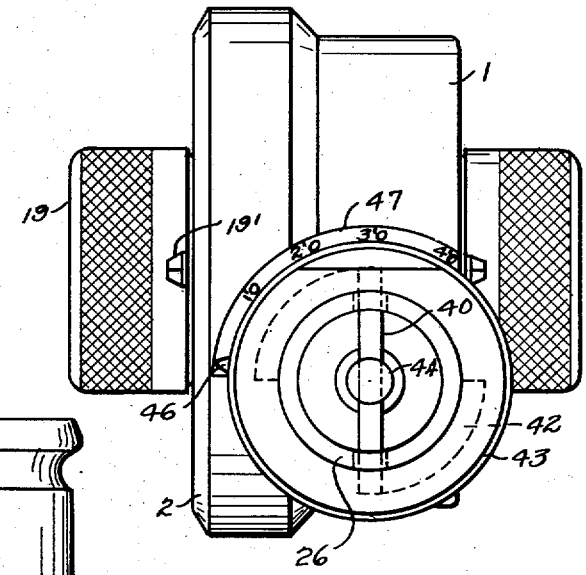
Fig. 1 is a top plan view of the present resuscitator looking down on the gas lead-in connection and regulating means associated therewith.
Figure 2:
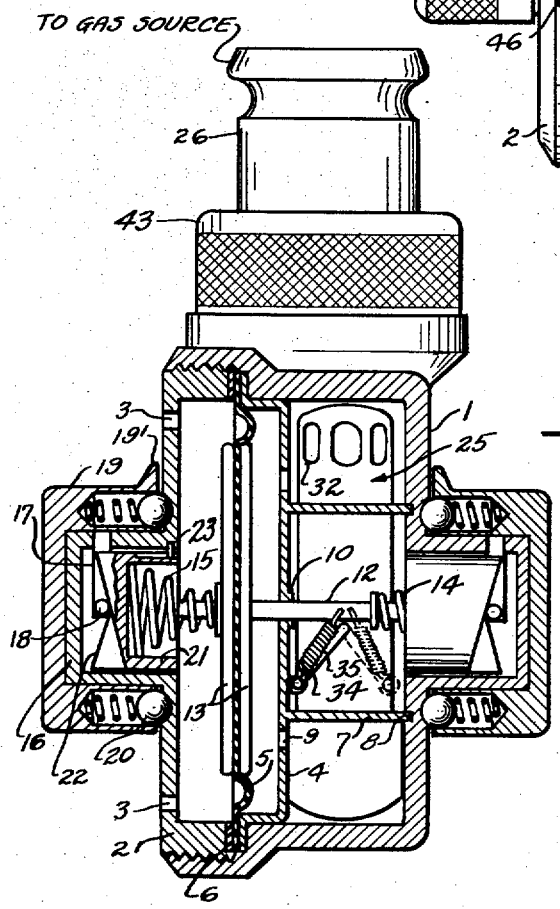
Fig. 2 is a vertical cross sectional view taken on the line 2—2 of Fig. 3.

Referring to Figs. 1 to 4 of the drawings the resuscitator will be described in detail. The main body 1 is of generally cylindrical shape and is closed at one end by a screw threaded cap or cover plate 2 having small openings 3 therein. An annular shoulder within the body provides a seat for a circular wall member 4, a circular diaphragm 5 and a circular gasket 6 in series and these elements are retained by the screw cap 2. The wall member 4 includes a cylindrical extension 7 having its rim edge seated in a shallow groove formed in the body 1 at 8. Outwardly of the extension 7 the wall member 4 is pierced by a series of openings 9. A small cylindrical boss 10 at the center of the wall member 4 provides a guide for a slidable valve actuating rod or stem 12 extending through the center of the diaphragm 5 and rigidly fixed to a pair of diaphragm supporting plates or disks 13. At opposite ends of the rod 12 are similar compression springs 14 and 15 to provide light resistance to endwise movement of the rod 12 The adjusting means for the springs 14 and 15 are identical, so that only one such adjusting means need be described. Adjacent to the spring 15 the screw cap 2 is provided with a cup-like extension 16 having opposite slots 17 extending through a substantial part of the circumference and receiving a transverse pin 18, the opposite ends of which are anchored in a rotatable knob 19 fitting over the extension or boss 16. Ball detents 20 in the walls of the knob bear on screw cap 2 to give frictional adjusting action to the knob as the detents snap into suitable indentations. Slidably mounted in the hollow extension 16 is a spring abutment member 21 having opposite and similar cam portions 22 which cooperate with transverse pin 18 so as to produce inward and outward movement of the spring abutment member as the knob 19 is rotated. As seen in Figs. 1 and 2 the knob 19 carries a pointer 19′ which may be set with respect to suitable indicia to indicate the pressure response of the resuscitator as it cycles back and forth between suction and pressure phases of the resuscitation cycle. A suitable pin or other spline element 23 may be provide to maintain the abutment member 21 in non-rotatable relation with respect to hollow extension or boss 16. The compressive effect of spring 15 determines the maximum positive pressure applied to the patient during the inhalation phase of the resuscitation cycle, while the compressive effect of spring 14 determines the minimum negative pressure which obtains in the exhalation phase of the cycle. Suggested pressure ranges for these phases are 0 to +8 inches of water for the inhalation phase and 0 to −3 inches of water for the exhalation phase. Suitable indicia adjacent to the spring adjusting knobs provide a calibrated scale for these pressure ranges. The maximum inlet pressure of the gas reaching the fitting 26 will usually be held to the maximum positive pressure used in resuscitation, for example about +10 inches of water.

Figure 3:
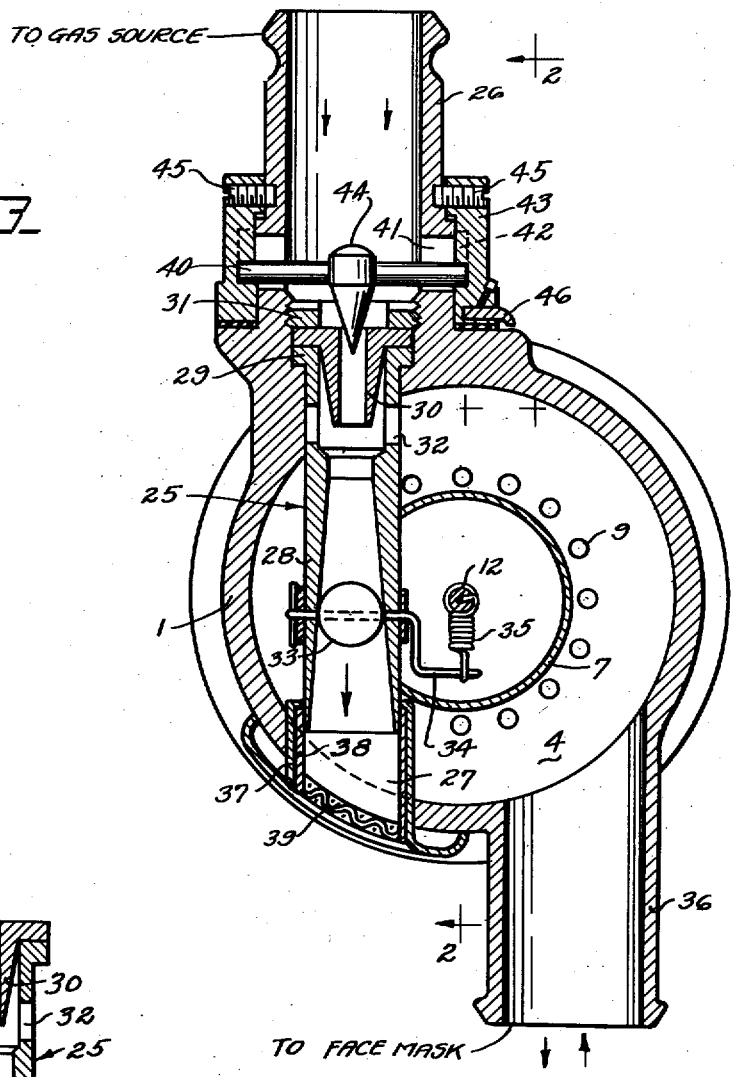
Fig. 3 is a transverse cross sectional view through the resuscitator and showing the aspirator in longitudinal cross section.
Figure 4:
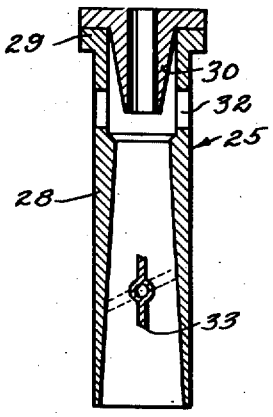
Fig. 4 is a longitudinal cross section taken through the aspirator and associated control valve.

Referring to Figs. 3 and 4, there is shown an aspirator assembly 25 which extends through the main body 1 at one side of a central location and coaxial with respect to the gas inlet fitting 26 and a gas outlet or discharge passage 27. The aspirator includes a tube 28 having an annular flange 29 at the inlet end seated against an annular shoulder in the resuscitator body 1. Seated on the flange 29 is a flanged nozzle element 30 and the contacting flanges are held in place as shown by a threaded ring 31 which includes wrench-receiving radial slots. The interior of the tubular member 28 is of flared cross section to provide a diffuser section in the aspirator extending almost to the outlet of nozzle 30. Laterally opening gas ports 32 in the tube 28 adjacent to the outlet of nozzle 30 provide communication to the interior of body 1 and particularly to an annular space between the wall member 4 and the end wall of body 1 remote from the diaphragm 5 (see Fig. 2). A butterfly valve 33 in the tube 28 is rigidly connected to a crankshaft 34 having an offset end situated at one side of the rod 12 and connected thereto by an actuating spring 35. As the rod 12 is shuttled back and forth by action of the diaphragm 5, the spring 35 moves from one side to the other of the axis of rotation of crankshaft 34 thus causing the valve 33 to snap to open or closed position with a sudden movement (see Fig. 2). The solid line positions of the spring, crankshaft and valve correspond to the open position of the valve wherein the aspirator 25 is effective to pull a vacuum in the annular space leading to the tubular fitting 36. This brings about the exhalation phase of the resuscitation cycle, since the fitting 36 normally carries a tube leading to the face mask. When the valve 33 moves to closed position, the gas from nozzle 30 can only spill out through ports 32 to provide positive gas flow through fitting 36 to the face mask. The annular wall portion 7 provides means to form a definite gas channel from the ports 32 to the fitting 36 and vice versa. This protects the moving parts, such as stem 12, spring 35 and crankshaft 34 from moisture exhaled from the patient's lungs. One objection to moisture as it relates to moving parts is the danger of freezing up at low temperatures. The operation will be more fully described below.

The outlet end of tube 28 extends into a flanged tubular element 37 having removable liner 38 which carries a screen 39 across the outer end to prevent foreign bodies and extraneous material, such as packing, from entering the resuscitator. The fitting 26 for connection with a source of gas under pressure, such as a cylinder of oxygen, has mounted therein a flow regulating valve comprising a transverse rod 40 extending into longitudinal slots 41 in the fitting 26 and also into similar cam slots 42 in the rotatable collar 43. The rod 40 carries a tapered valve member 44 adapted to enter the outer end of nozzle 30 and thus regulate the size of the annular passage between the valve member and the nozzle opening. A pair of screws 45 threaded into the collar 43 have inner ends riding in a circular groove in fitting 26 to prevent endwise movement of collar 43 but still permit free rotation thereof. A pointer 46 on the collar 43 serves to indicate by its position with relation to the scale 47, the flow rate through the regulating valve and into the nozzle 30. The suggested scale of values for the flow rate is from 0 to 40 liters per minute. Ordinarily the valve will only be closed completely when the resuscitator is not in use but the wide range of flow rates will adapt the device for use on people of all ages and all possible basic metabolic rates. Furthermore the flow rate in any given case will determine the cycling rate of the resuscitator, since the rate of gas flow will determine how fast the patient's lungs fill to capacity and how fast the patient's lungs are emptied of gas, moisture and waste products.

RESUSCITATOR OPERATION

The operation of the resuscitator will be explained by reference to Figs. 1 to 4. Referring first to Fig. 2, the valve actuating diaphragm 5 is here shown in an approximate mid-position and since the butterfly valve 33 is open the aspirator is drawing gas from the interior of the resuscitator. Thus the diaphragm is being pulled toward the right in Fig. 2. The effect of spring 15 is no longer appreciable but the negative pressure spring 14 is resisting further movement of the rod 12 toward the right. Now it will be seen that the setting of spring 14 will effectively determine how low the pressure goes before the coil spring 35 swings to the right past the crank arm 34 and causes the crank arm and the valve 33 to snap to the valve closing position and start the inhalation or positive pressure phase of the resuscitation cycle. Now with the valve 33 closed the incoming gas will flow from ports 32 into the resuscitator body and thence around the flow channel previously described to the outlet fitting 36. As the patient's lungs fill up with fresh gas the positive pressure in the resuscitator will slowly increase to cause the diaphragm 5 to move toward the left, thus moving the rod 12 and bringing the overcenter coil spring 35 to the dotted line position with the crank arm 34 still in the dotted line or valve closed position. Now the compression spring 14 is no longer producing any appreciable endwise pressure on the rod 12 but the positive pressure spring 15 is resisting further movement of the rod 12 toward the left. Thus it will be seen that the setting of spring 15 will determine how high the pressure goes before the coil spring 35 swings past the crank arm 34 and causes the crank arm and valve 33 to snap to the valve opening position and thereby start the exhalation or negative pressure phase of the resuscitation cycle. The spring 35 is shown in two positions, each approaching the critical snap-over relation, with respect to the crank arm 34 (see Fig. 2). The crank arm is shown in its two extreme positions, the full line position being the valve open position (see Figs. 2, 3 and 4) and the dotted line position being the valve closed position. In the first position, the contact of the arm and wall 4 provides a definite stop action and in the second position the contact of the valve 33 with the walls of tube 28 provides a definite stop action. As noted previously the adjustable inlet valve determines the flow rate for a given subject and also determines at the same time the cycling rate of the resuscitator. In practice a table of values is furnished with the resuscitator to show the desired setting of the inlet valve for people of various ages and more particularly for people of various sizes. In some cases the values are varied from the normal, as for instance in applying the resuscitator to persons who have absorbed noxious fumes. Here a higher flow rate will aid in eliminating from the blood some of the undesirable dissolved gases. While the exhalation phase of the resuscitation cycle will preferably proceed until there is a slight negative pressure in the device, this practice is not always recommended. Some authorities do not recommend the use of negative pressures in resuscitation or artificial respiration because of the tendency to cause adhesion of lung tissues and partial collapse of bronchial tubes.

RESUSCITATION SYSTEM

Referring now to Fig. 5 there is shown one possible resuscitation system or hook-up of general application. The resuscitator as described above is shown in exterior end view showing the spring adjusting knob 19 mounted on the screw cap 2. The fitting 36 is connected to the face mask 50, which is adapted to fit over the mouth and nose of the patient and may be held in place by hand or by suitable straps. At the face contacting edges of the mask there is provided a flexible tube 51 connected to the interior of the mask by means of a one-way valve 52, arranged so that the maximum pressure in the mask will be developed in the tube 51 but will not leak back into the mask.

The gas inlet fitting 26 is connected to a conduit 53 connected through a shut-off valve 54 and pressure relief valve 55 to a blower 56. The latter is provided with an air inlet screen 57 and the rotor 58 is mounted on a shaft 59 extending into an adjacent impulse turbine unit 60. The shaft 59 also includes a non-circular end portion 61 which may be connected in an emergency to an electric motor or other power source in case the motive power for the turbine 60 fails. In normal operation the turbine 60 is operated by atmospheric air entering at the nozzle 62 and impinging on the turbine rotor 60'. The flow of atmospheric air against the turbine wheel is brought about by connecting the turbine casing to a jet pump 63 or other vacuum pump. The jet pump is operated by passing a stream of water therethrough from a water tap 64 and the water after passing out of the pump flows into a suitable drain or sink 65. A second source of gas is conducted into the tube 53 by a conduit connected by way of a shut-off valve 66 and a reduction valve 67 to an oxygen tank or bottle 68. As will be understood the oxygen may be under very high pressure in the bottle 68 and in order to bring the pressure at the resuscitator inlet 26 down to about +10 inches of water there must be provided an efficient reduction valve preferably mounted directly on the outlet tube of tank or bottle 68.

The system illustrated in Fig. 5 should afford reasonable safety because of the alternative sources of resuscitating gas. In the illustration, the source of compressed air from blower 56 is connected to the resuscitator since the valve 54 is open at the same time the valve 66 is closed. The pressure relief valve 55 near the blower is for the purpose of maintaining a predetermined maximum pressure in the conduit 53, for instance about +10 inches of water. While pure oxygen having a minor percentage of carbon dioxide mixed therein is the preferred gas, compressed air will always provide a satisfactory substitute. In some cases carbon dioxide is added continuously to the flowing oxygen from a separate bottle equipped with a metering valve.

The embodiment of the invention herein shown and described is to be regarded as illustrative only and it is to be understood that the invention is susceptible of variations, modifications and changes within the scope of the appended claims.

I claim:

1. A resuscitator comprising, a housing defining a gas receiving chamber, said housing being provided with a port adapted for connection with a mask, conduit means traversing said chamber, said conduit means being fitted at one end for attachment to a source of gas under pressure and the other end thereof defining a discharge port open to the ambient atmosphere, jet jump means within said conduit means and including a nozzle and an adjacent constriction spaced downstream from the nozzle, a rotatably mounted valve positioned between said constriction and said discharge port for opening and closing said conduit means, a crankshaft rigidly connected to said valve and extending outside of said conduit means, a valve actuating diaphragm in said housing communicating at one side with said gas receiving chamber, a slidably mounted rod secured centrally of said diaphragm, spring means extending laterally from said rod and connected to said crankshaft, port means in said conduit upstream from said constriction and connecting with said gas receiving chamber, whereby gas flowing into said conduit will alternately flow through said port means and to the lungs of a patient wearing said mask or flow through said jet pump to the ambient atmosphere as said valve is closed or opened respectively by action of said diaphragm, rod, spring means and crankshaft.

2. A resuscitator comprising, a housing defining a gas receiving chamber, said housing being provided with a port adapted for connection with a mask, conduit means traversing said chamber, said conduit means being fitted at one end for attachment to a source of a gas under pressure and the other end thereof defining a discharge port open to the ambient atmosphere, jet pump means within said conduit means and including a nozzle and an adjacent constriction spaced downstream from the nozzle, a rotatably mounted valve positioned between said constriction and said discharge port for opening and closing said conduit means, a crankshaft rigidly connected to said valve and including a crank arm portion outside of said conduit means, a valve actuating diaphragm in said housing communicating at one side with said gas receiving chamber, a slidably mounted rod secured centrally of said diaphragm and extending at a right angle with respect to said crankshaft, a coil spring connected between said rod and said crank arm portion and adapted to swing past said crankshaft to two opposite overcenter positions as said rod reciprocates by action of said diaphragm and as said valve is moved to closed and open positions, port means in said conduit upstream from said constriction and connecting with said gas receiving chamber, whereby gas flowing into said conduit will alternately flow through said port means and to the lungs of a patient wearing said mask or flow through said jet jump to the ambient atmosphere as said valve is closed or opened respectively by action of said diaphragm, rod, spring and crankshaft.

3. A resuscitator comprising, a housing defining a gas receiving chamber, said housing being provided with a port adapted for connection with a mask, conduit means traversing said chamber, said conduit means being fitted at one end for attachment to a source of gas under pressure and the other end thereof defining a discharge port open to the ambient atmosphere, jet pump means within said conduit means and including a nozzle and an adjacent constriction spaced downstream from the nozzle, a rotatably mounted valve positioned between said constriction and said discharge port for opening and closing said conduit means, a valve actuating diaphragm positioned transversely of said housing, a perforate transverse wall in said housing spaced from said diaphragm and having a tubular extension engaging one end of said housing away from said diaphragm, a rod slidably mounted through said transverse wall and extending axially through said tubular extension, means for securing said rod centrally of said diaphragm, a crankshaft rigidly connected to said valve and extending outside of said conduit means within said tubular extension, spring means connected between said rod and said crankshaft for actuating said valve from closed to open position and vice versa upon sliding movement of said rod in opposite directions, and port means in said conduit means upstream from said constriction and connecting with said gas receiving chamber.

4. A resuscitator comprising, a housing defining a gas receiving chamber, means providing a gas inlet into said housing, means providing a gas outlet from said housing into the ambient atmosphere, means providing a fitting on a wall of said housing connecting with said chamber and adapted for connection with a mask, an aspirator extending across said housing from said gas inlet to said gas outlet and including spill ports opening laterally from the aspirator into said gas receiving chamber, a rotatably mounted valve in said aspirator downstream from said ports, a crankshaft rigidly connected to said valve and extending outside of said aspirator, a slidably mounted rod in said housing extending at a right angle to said crankshaft, spring means extending laterally from said rod and connected to said crankshaft to assume overcenter positions at opposite sides of sand crankshaft as said valve is moved from closed to open positions, means responsive to changes in pressure in said chamber for moving said rod in opposite directions as the pressure in said chamber rises and falls, whereby a supply of gas flowing to said gas inlet will alternately flow through said ports and to the lungs of a patient wearing said mask or flow through said aspirator to the ambient atmosphere as said valve is closed or opened respectively.

5. A resuscitator as recited in claim 4, and further comprising, separate adjustable spring means bearing on opposite ends of said slidably mounted rod.

6. A resuscitator comprising, a housing defining a gas receiving chamber, means providing a gas inlet into said housing, means providing a gas outlet from said housing into the ambient atmosphere, means providing a fitting on a wall of said housing connecting with said chamber and adapted for connection with a face mask, an aspirator extending across said housing from said gas inlet to said gas outlet and including spill ports opening laterally from the aspirator into said gas receiving chamber, a movably mounted valve in said aspirator downstream from said ports, valve operating means connected to said valve and extending outside of said aspirator, a slidably mounted rod in said housing, means responsive to changes in pressure in said chamber for moving said rod in opposite directions as the pressure in said chamber rises and falls, spring means connected between said valve operating means and said rod to actuate said valve from closed to open position and vice versa as said rod is moved in opposite directions by the action of rising and falling pressure in said chamber, and separate adjustable [spring] *biasing* means at opposite ends of said rod for biasing said rod in opposite directions.

7. *A resuscitator comprising, a housing defining a gas receiving chamber, means providing a gas inlet into said housing, means providing a gas outlet from said housing into the ambient atmosphere, means providing a fitting on a wall of said housing connecting with said chamber and adapted for connection with a face mask, an aspirator extending across said housing from said gas inlet to said gas outlet and including spill ports opening laterally from the aspirator into said gas receiving chamber, a movably mounted valve in said aspirator downstream from said ports, valve operating means connected to said valve and extending outside of said aspirator, a reciprocably mounted means in said housing, means responsive to changes in pressure in said chamber for moving said reciprocably mounted means in opposite directions as the pressure in said chamber rises and falls, means connected between said valve operating means and said reciprocably mounted means to actuate said valve from closed to open position and vice versa as said reciprocably mounted means is moved in opposite directions by the action of rising and falling pressure in said chamber, and separate adjustable biasing means acting in opposition on said reciprocably mounted means for biasing the latter means in opposite directions.*

HENRY SEELER.

No references cited.